US012606514B2

(12) United States Patent
Lee et al.

(10) Patent No.: US 12,606,514 B2
(45) Date of Patent: *Apr. 21, 2026

(54) ISOMERIZATION METHOD OF CYCLOHEXANE DICARBOXYLIC ACID

(71) Applicant: HANWHA SOLUTIONS CORPORATION, Seoul (KR)

(72) Inventors: Jong Kwon Lee, Daejeon (KR); Namjin Jang, Daejeon (KR); Eun Jeong Kim, Daejeon (KR); Sun Uk Lee, Daejeon (KR)

(73) Assignee: HANWHA SOLUTIONS CORPORATION, Seoul (KR)

( * ) Notice: Subject to any disclaimer, the term of this patent is extended or adjusted under 35 U.S.C. 154(b) by 641 days.

This patent is subject to a terminal disclaimer.

(21) Appl. No.: 17/781,809

(22) PCT Filed: Oct. 27, 2020

(86) PCT No.: PCT/KR2020/014713
§ 371 (c)(1),
(2) Date: Jun. 2, 2022

(87) PCT Pub. No.: WO2021/112405
PCT Pub. Date: Jun. 10, 2021

(65) Prior Publication Data
US 2022/0371981 A1 Nov. 24, 2022

(30) Foreign Application Priority Data
Dec. 5, 2019 (KR) ........................ 10-2019-0160692

(51) Int. Cl.
*C07C 51/353* (2006.01)
*B01J 21/06* (2006.01)
(Continued)

(52) U.S. Cl.
CPC ........... *C07C 51/353* (2013.01); *B01J 21/066* (2013.01); *B01J 35/613* (2024.01); *B01J 35/633* (2024.01);
(Continued)

(58) Field of Classification Search
CPC ..... C07C 51/353; B01J 35/647; B01J 35/613; B01J 35/633; B01J 35/651; B01J 21/066; B01J 35/70
See application file for complete search history.

(56) References Cited

U.S. PATENT DOCUMENTS 5,286,903 A 2/1994 Irick, Jr.

FOREIGN PATENT DOCUMENTS

CN 101433863 A * 5/2009 .............. B01J 21/12
JP H08502747 A 3/1996
(Continued)

OTHER PUBLICATIONS

KR101208050B1 (Lee et al.; English language machine translation) (Year: 2012).*
(Continued)

*Primary Examiner* — Amy C Bonaparte
*Assistant Examiner* — Derek Rhoades
(74) *Attorney, Agent, or Firm* — Harvest IP Law, LLP

(57) ABSTRACT
The present disclosure relates to an isomerization method of a cyclohexane dicarboxylic acid (CHDA) and, more specifically, to a method for preparing a trans-cyclohexane dicarboxylic acid (t-CHDA) from a cis-cyclohexane dicarboxylic acid (c-CHDA) by means of catalytic isomerization. Particularly, an embodiment of the present disclosure provides a method for preparing, in high efficiency and high yield and at a low cost, a CHDA having a high t-CHDA content from a CHDA mainly containing c-CHDA, by using an isomerization catalyst containing zirconia and having a BET specific surface area of 50 $m^2/g$ or more.

11 Claims, 3 Drawing Sheets

(51) Int. Cl.
     B01J 35/61          (2024.01)
     B01J 35/63          (2024.01)
     B01J 35/64          (2024.01)
     B01J 35/70          (2024.01)

(52) U.S. Cl.
     CPC ........... B01J 35/647 (2024.01); B01J 35/651
          (2024.01); B01J 35/70 (2024.01); *B01J*
          *2235/15* (2024.01)

(56)           References Cited

FOREIGN PATENT DOCUMENTS

| JP | WO1998009727 A1 * | 3/1998 | ............ B01J 27/053 |
|---|---|---|---|
| JP | 2000191602 A | 7/2000 | |
| JP | 2001151716 A | 6/2001 | |
| KR | 20050100941 A | 10/2005 | |
| KR | 101208050 B1 | 12/2012 | |
| KR | 20190038062 A | 4/2019 | |
| KR | 1020190076389 A | 7/2019 | |
| WO | 9410124 A1 | 5/1994 | |
| WO | 2006119549 A1 | 11/2006 | |

OTHER PUBLICATIONS

Korean J. Chem. Eng. 2001, 18, 992-999 (Jung et al.) (Year: 2001).*
CN101433863A (Xu et al.; English language machine translation).*
J. Catal. 1996, 160, 279-289 (Lonyi et al.) (Year: 1996).*
International Search Report dated Feb. 1, 2021.

* cited by examiner

[FIG. 1]
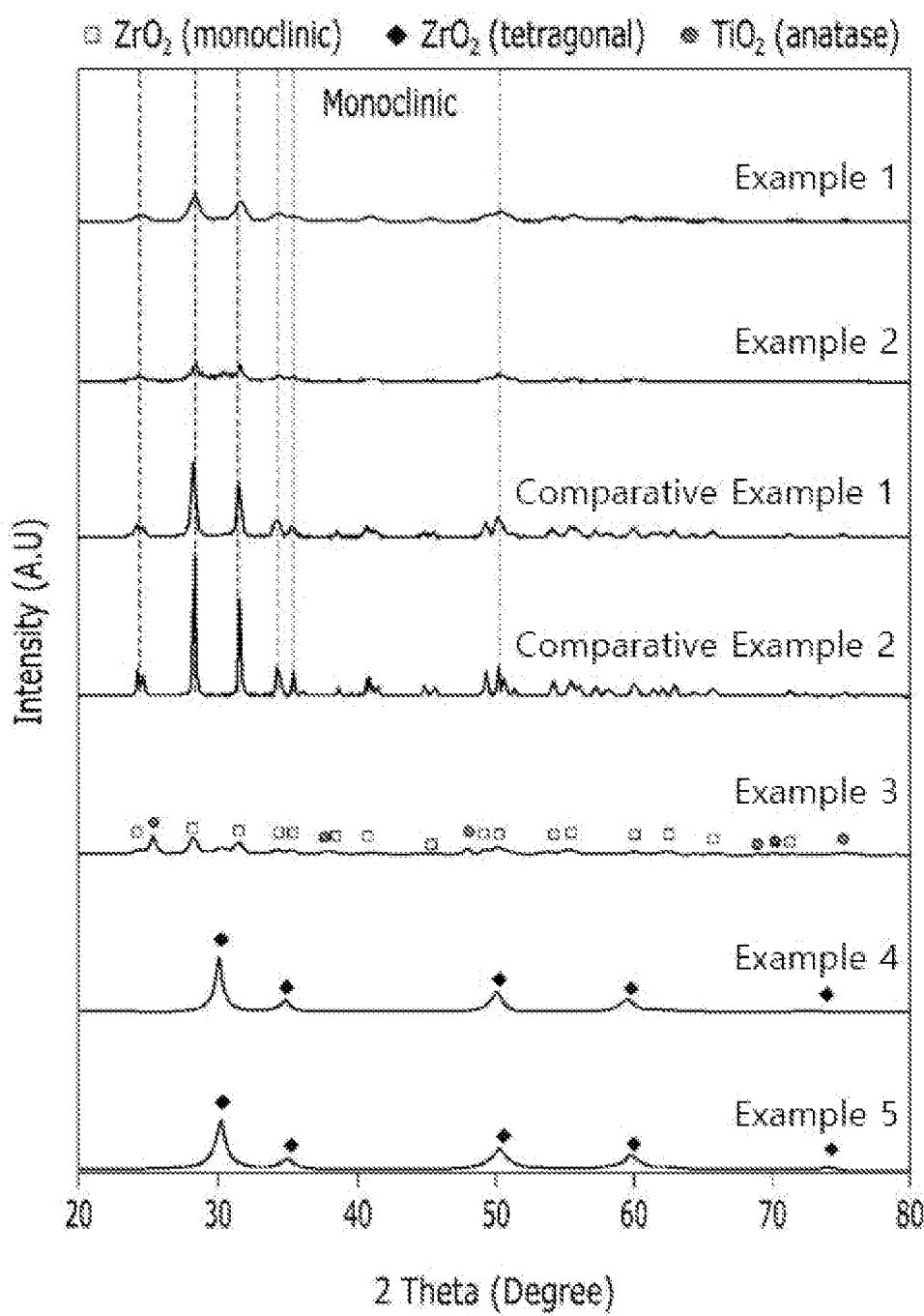

[FIG. 2]
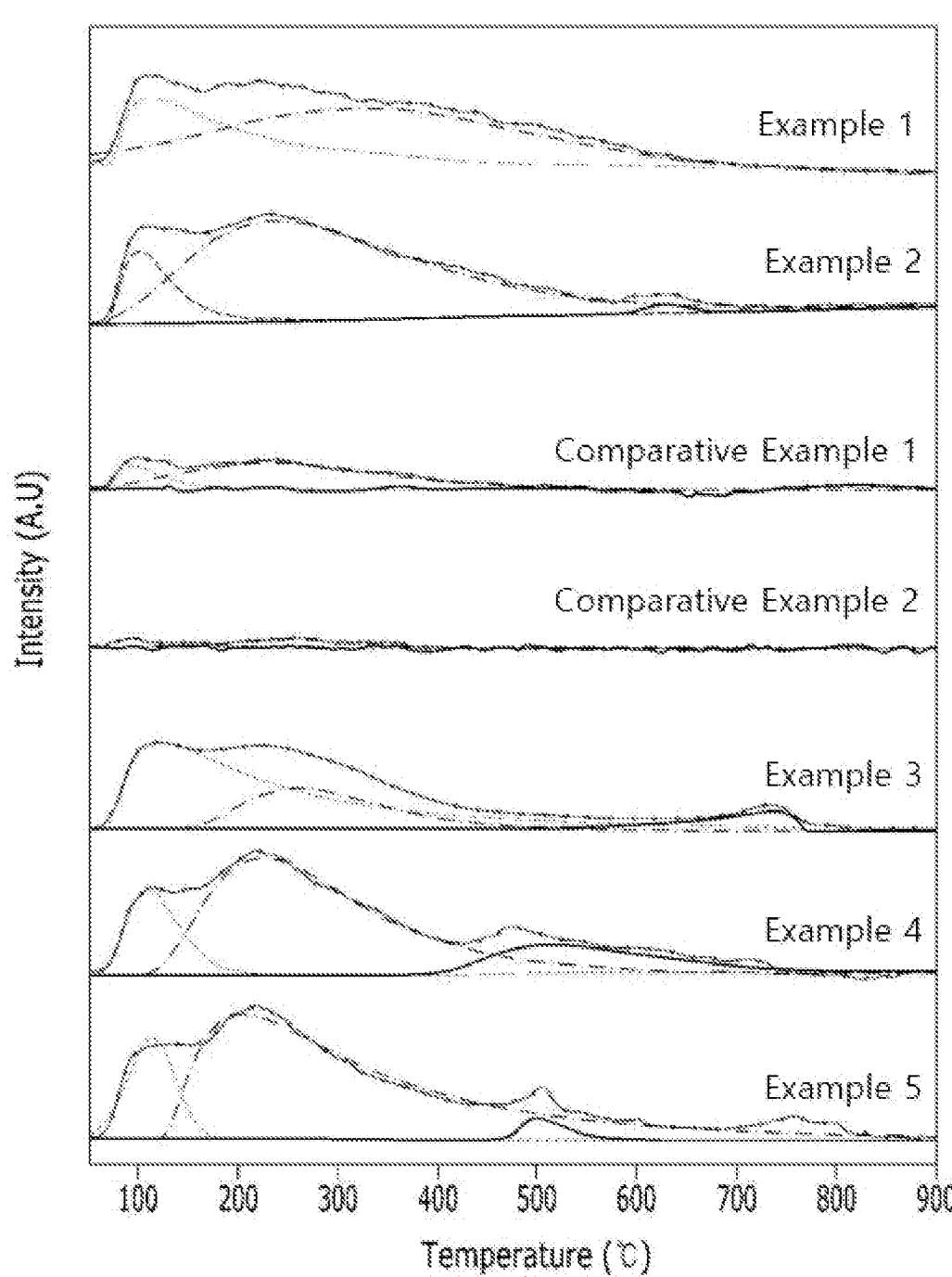

[FIG. 3]
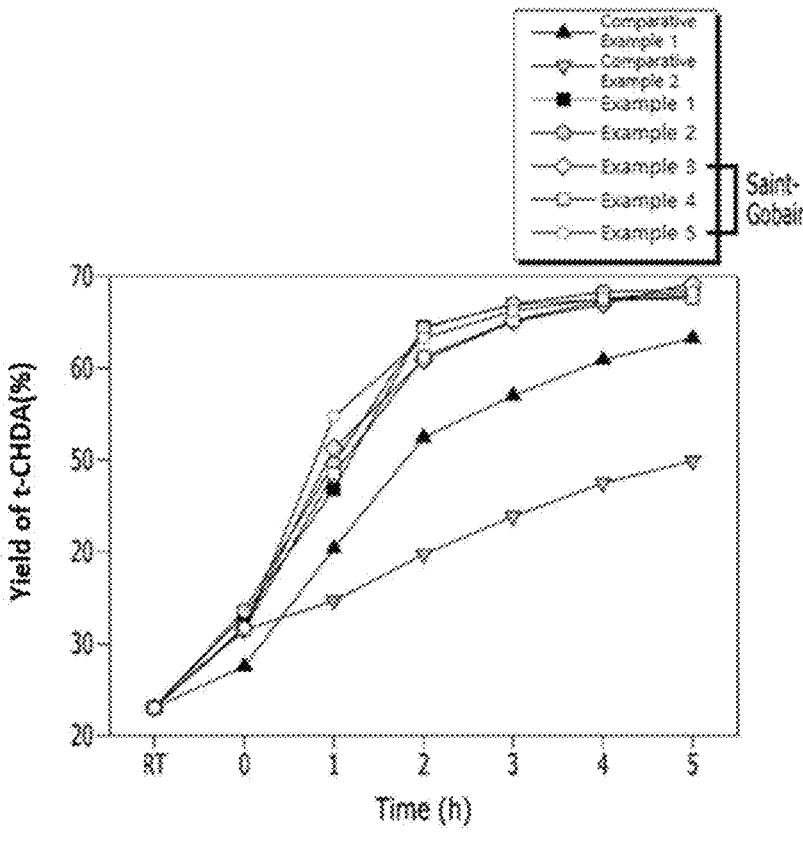

ISOMERIZATION METHOD OF CYCLOHEXANE DICARBOXYLIC ACID

CROSS-REFERENCE TO RELATED APPLICATION(S)

This application is a National Stage of International Application No. PCT/KR2020/014713 filed on Oct. 27, 2020 claiming the benefit of Korean Patent Application No. 10-2019-0160692 filed on Dec. 5, 2019 with the Korean Intellectual Property Office, the content of which is incorporated herein by reference in its entirety.

The present disclosure relates to an isomerization method of a cyclohexane dicarboxylic acid (CHDA) and more particularly to a method for preparing a trans-cyclohexane dicarboxylic acid (t-CHDA) from a cis-cyclohexane dicarboxylic acid (c-CHDA) by means of catalytic isomerization.

BACKGROUND ART

Cyclohexanedicarboxylic acid (CHDA) is widely used as a raw material for pharmaceuticals, synthetic resins, synthetic fibers, or dyes, and particularly, trans-cyclohexanedicarboxylic acid (t-CHDA) is used as a raw material for preparing resins or fibers for which heat resistance, weather resistance, and strength characteristics are required. Therefore, CHDA having a high concentration of t-CHDA is required.

Generally, CHDA is prepared by a method of hydrogenating terephthalic acid (TPA) or hydrogenating a benzene ring of a TPA derivative. As an example, in the case of a method of hydrogenating the benzene ring of the TPA derivative, there is mentioned a method of converting the carboxyl group of TPA to a metal salt such as a sodium salt or various esters to hydrogenate a benzene ring (nucleus hydrogenation) or a method of nucleus-hydrogenating a carboxyl group.

However, in these methods, the isomers are produced by hydrogenation of the benzene ring of TPA, and the resulting CHDA is in the form of a mixture of c-CHDA and t-CHDA. The concentration of t-CHDA in the obtained CHDA depends on the reaction conditions, but is as low as less than 50%.

Thus, various methods for increasing the concentration of t-CHDA in CHDA are being studied, and the most studied method among them is a thermal isomerization method.

However, since this method is heated to a temperature higher than the melting point of t-isomer, the obtained t-CHDA is very hard and thus difficult to handle. Moreover, there is a problem that t-CHDA having a high purity of 98% can be finally obtained only when t-CHDA is heat-treated and then recrystallized from water using activated carbon.

In addition to this, several methods for preparing CHDA with a high concentration of t-CHDA have been proposed, but a method which is advantageous in all aspects such as reaction efficiency, yield, and processability has not yet been confirmed.

DETAILED DESCRIPTION OF THE INVENTION

Technical Problem

It is an object of the present disclosure to provide a method for catalytic isomerization of CHDA, which can prepare, in high efficiency and high yield and at a low cost, a CHDA having a high t-CHDA content from a CHDA mainly containing c-CHDA

Technical Solution

According to an embodiment of the present disclosure, there is provided a method for preparing, in high efficiency and high yield and at a low cost, a CHDA having a high t-CHDA content from a CHDA mainly containing c-CHDA, by using an isomerization catalyst containing zirconia and having a BET specific surface area of 50 $m^2$/g or more.

Advantageous Effects

By the isomerization method of a CHDA according to the present disclosure, the trans/cis ratio in CHDA can be easily adjusted. Thereby, CHDA rich in the trans isomer can be prepared from CHDA rich in the cis isomer.

BRIEF DESCRIPTION OF THE DRAWINGS

FIG. 1 is a graph showing the results of X-ray diffraction analysis for each catalyst of Examples and Comparative Examples (Test Example 1).

FIG. 2 is a graph showing the results of the ammonia-temperature programmed desorption ($NH_3$-TPD) analysis for each catalyst of Examples and Comparative Examples (Test Example 1).

FIG. 3 is a graph showing the results of evaluating the yield of t-CHDA according to the reaction temperature during the isomerization reaction using each catalyst of Examples and Comparative Examples.

DETAILED DESCRIPTION OF THE EMBODIMENTS

The technical terms used herein is only to explain embodiments and is not intended to limit the scope of the present disclosure. The singular forms "a," "an" and "the" are intended to include plural forms, unless the context clearly indicates otherwise. It should be understood that the terms "comprise," "include", "have", etc. are used herein to specify the presence of stated features, integers, steps, components or combinations thereof, but do not preclude the presence or addition of one or more other features, integers, steps, components, or combinations thereof.

Although the present disclosure may have various forms and various modifications may be made thereto, specific examples will be exemplified and explained in detail below. However, it is not intended to limit the present disclosure to specific disclosure, and it should be understood that the present disclosure includes all the modifications, equivalents or replacements thereof without departing from the spirit and technical scope of the present disclosure.

Now, the isomerization method and isomerization catalyst of a CHDA according to specific embodiments of the present disclosure will be described in more detail.

Isomerization Method of Cyclohexane Dicarboxylic Acid

According to an embodiment of the present disclosure, there is provided a method for preparing, in high efficiency and high yield and at a low cost, a CHDA having a high t-CHDA content from a CHDA mainly containing c-CHDA, by using an isomerization catalyst containing zirconia and having a BET specific surface area of 50 $m^2$/g or more.

The isomerization reaction of a CHDA according to an embodiment of the present disclosure utilizes a reaction mechanism in which the isomerization reaction proceeds with c-CHDA adsorbed onto the isomerization catalyst and then the product isomerized by t-CHDA is desorbed, and thereby corresponds to a catalytic isomerization method capable of preparing t-CHDA in high efficiency and high yield while reducing the process cost, as compared with the previously known hydrogenation method of TPA, a thermal isomerization method, and the like.

Here, the interaction between c-CHDA and the isomerization catalyst, the adsorption of the reactant and the isomerization catalyst, and the desorption of the product and the isomerization catalyst after completion of the reaction greatly affect the isomerization reaction efficiency and the yield of the isomerized product, whereby the isomerization catalyst must be able to exhibit an appropriate strength of adsorption and desorption for both reactants and products, respectively.

Essential Components of the Catalyst and BET Specific Surface Area

Specifically, the isomerization reaction of a CHDA according to an embodiment of the present disclosure exhibits excellent interaction with c-CHDA and thus contains zirconia capable of contributing to the improvement of reaction efficiency, as compared with inorganic oxides such as silica, or ceria.

Additionally, t-CHDA, which is a product after completion of the isomerization reaction, is strongly adsorbed onto the isomerization catalyst and thus is not separated, whereby unlike alumina, magnesia, etc., which reduce the yield, zirconia can exhibit appropriate adsorption and desorption power for reactants and products, respectively, during isomerization reaction without special surface treatment or modification.

Moreover, since zirconia has a high melting point and thus exhibits excellent fire resistance, and is chemically very stable, it has little possibilty of causing a side reaction even when used as a catalyst for an isomerization reaction.

However, even if zirconia is contained, it is necessary to consider that reaction efficiency and yield of t-CHDA may vary depending on the physical properties thereof.

Of course, it is a well-known fact that the larger the BET specific surface area of a catalyst, the larger the amount of reactants are adsorbed, which contributes to the improvement of reaction efficiency.

However, in the isomerization reaction of CHDA, the BET specific surface area characteristics of the catalyst that can significantly improve the reaction efficiency and yield of t-CHDA have not been presented so far. Thus, in an embodiment of the present disclosure, the optimal BET specific surface area characteristics confirmed through actual tests will be presented.

Specifically, when the isomerization reaction of CHDA according to the one embodiment was actually tested, it was confirmed that when an isomerization catalyst with a BET specific surface area of 50 m²/g or more is used while containing zirconia, the initial reaction efficiency is significantly improved, and the yield of t-CHDA is also significantly increased.

More specifically, as a catalyst having a wider BET specific surface area in the range of 50 m²/g or more, 60 m²/g or more, 70 m²/g or more, or 80 m²/g or more is used while containing zirconia, a larger amount of c-CHDA during the isomerization reaction of CHDA can be adsorbed and reacted onto the catalyst, thereby improving the initial reaction efficiency and the yield of t-CHDA.

The upper limit of the BET specific surface area of the isomerization catalyst is not particularly limited, but considering that desorption of the product (i.e., t-CHDA) may be difficult if the specific surface area is too high, it is controlled in a range of 200 m²/g or less, 180 m²/g or less, 160 m²/g or less, or 140 m²/g or less.

Taken together, the isomerization method of CHDA according to an embodiment of the present disclosure includes a step of heat-treating a mixed solution prepared by mixing a cyclohexane dicarboxylic acid containing a cis isomer, water, and an isomerization catalyst to isomerize the cis isomer to a trans isomer, wherein the isomerization catalyst includes zirconia and uses a BET specific surface area of 50 m²/g or more, thereby improving the initial efficiency of the reaction and the yield of t-CHDA.

In addition, by further adjusting the composition, pore characteristics, acid characteristics, and the like of the isomerization catalyst, the initial reaction efficiency and the yield of t-CHDA can be further improved, and the description thereof will be given in detail.

Acid Characteristics of Catalyst

In the isomerization reaction of CHDA according to the one embodiment, the amount of acid sites possessed by the isomerization catalyst may affect the reactivity of the isomerization reaction of CHDA, the yield of t-CHDA resulting therefrom, and the like.

Specifically, as the amount of weak acid sites and the amount of middle acid sites possessed by the isomerization catalyst are larger, and the total amount of acid sites resulting therefrom is larger, the isomerization reaction of CHDA according to the one embodiment can be further promoted, thereby improving the final yield of t-CHDA.

A commonly known method for analyzing acid sites of a catalyst is an ammonia-temperature programmed desorption ($NH^3$-TPD) analysis, in which the amount of ammonia desorbed under specific conditions is measured to plot a temperature programed desorption curve, and then a peak appearing on the temperature programed desorption curve can be grasped as acid sites.

In the case of the isomerization catalyst, two or three peaks can be exhibited depending on the strength of acid. Here, this is classified into weak, middle, and strong acid sites from the low temperature region, and the amount of $NH_3$ desorbed at each acid site can be determined from the area of each peak.

According to actual tests about this, it was confirmed that the more catalysts containing zirconia, having a BET specific surface area of 50 m²/g or more, and having the total amount of acid sites of 400 umol/$g_{cat}$ or more, 500 umol/$g_{cat}$ or more, 600 umol/$g_{cat}$ or more, 700 umol/$g_{cat}$ or more, or 750 umol/$g_{cat}$ or more, are used, the yield of t-CHDA resulting from the isomerization of CHDA is improved.

Here, as the amount of weak acid sites and the amount of middle acid sites of the isomerization catalyst are larger and the total amount of acid sites resulting therefrom is larger, it can contribute to proceeding the isomerization reaction of CHDA at a lower reaction temperature and achieving a higher yield of t-CHDA (about 65% or more).

Specifically, when the isomerization catalyst is composed of acid sites such that, based on the total amount of acid sites (100 mol %) measured by an ammonia-temperature programmed desorption ($NH_3$-TPD), the amount of weak acid sites with an acid site desorption temperature of 50 to 150° C. is 5 to 75 mol %, specifically 10 to 70 mol %, the amount of middle acid sites with an acid site desorption temperature of 150 to 450° C. is 15 to 95 mol %, specifically 20 to 90 mol %, and the amount of strong acid sites with an acid site desorption temperature of 450° C. or more corresponds to the rest, the isomerization reaction promotion of CHDA, higher yield of t-CHDA, and the like can be achieved at a lower reaction temperature, as compared to the case where this is not satisfied.

Catalyst Crystallinity and Additional Component

As mentioned above, in the isomerization reaction of CHDA according to an embodiment, the BET specific surface area and acid characteristics can have a greater effect on the reaction efficiency and the yield of t-CHDA, rather than the crystallinity of the isomerization catalyst, the pore volume inside the isomerization catalyst and the average pore size.

Specifically, zirconia may have various crystal structures of monoclinic, tetragonal, or hexagonal systems, and considering only thermal and chemical stability, zirconia having a monoclinic crystal structure would have to be selected as a catalyst.

However, even if the crystal structure of zirconia, which is an essential component, is not a monoclinic system, and/or further contains the additional component, as long as an isomerization catalyst that satisfies the BET specific surface area and the total amount of acid sites presented in the one embodiment is used, there are disadvantages in thermal and chemical stability, but the fact remains that it exhibits excellent initial reaction efficiency and can achieve high t-CHDA yields.

In this regard, the zirconia, which is an essential component of the isomerization catalyst, may be monoclinic zirconia, tetragonal zirconia, or a mixture thereof.

Additionally, the isomerization catalyst may further include a heterogeneous transition metal oxide as an additional component while containing zirconia as an essential component. Here, the heterogeneous transition metal oxide may be titania, lantania, yttria, or a mixture thereof.

The titania, lanthania, and yttria, which are exemplified as the additional components, are excellent in chemical and material stability, respectively, and exhibit sufficient interaction with the reactants, thereby exhibiting a superior catalytic effect during CHDA isomerization reaction.

Specifically, titania may have a crystal structure of anatase, rutile and brookite, and lanthania and yttria may each have a crystal structure of monoclinic system, tetragonal system, hexagonal system or cubic system.

Although not particularly limited thereto, anatase titania, tetragonal lanthania, and tetragonal yttria can be used in consideration of the ease of catalyst preparation and the catalytic effect on the CHDA isomerization reaction.

The form in which the additional component is contained in the isomerization catalyst is not particularly limited, and may be mixed or compounded with zirconia, which is an essential component. For example, when the additional component is compounded with zirconia, which is an essential component, the isomerization catalyst may be a titania-zirconia composite, a lanthania-zirconia composite, a yttria-zirconia composite, or a mixture thereof.

However, not only when only essential components are contained alone in the isomerization catalyst, but also when additional components are further contained, it goes without saying that the BET specific surface area should satisfy 50 $m^2/g$ or more, and optionally, the total amount of acid sites measured by an ammonia-temperature programmed desorption ($NH_3$-TPD) method should satisfy 400 $umol/g_{cat}$ or more.

According to the actual test results, it was confirmed that when using a catalyst that contains a titania-zirconia composite, a lanthania-zirconia composite, or a yttria-zirconia composite, wherein the BET specific surface area and the total amount of acid sites satisfy each of the above ranges, it can achieve initial reaction efficiencies and yields of t-CHDA equal to or better than when only zirconia is contained alone and the BET specific surface area and the total amount of acid sites satisfy each of the above ranges.

When the additional component is contained in the isomerization catalyst, the content thereof may be 1 to 50% by weight, specifically 5 to 45% by weight. However, as described above, in the initial reaction efficiency and yield of t-CHDA, the BET specific surface area and acid characteristics of the catalyst are more important than the content of additional components in the isomerization catalyst.

Internal Ore Volume and Diameter of Catalyst

The isomerization catalyst may be a porous catalyst containing a plurality of pores therein.

At this time, the volume of pores in the isomerization catalyst may be 0.05 $cm^3/g$ or more to 1.5 $cm^3/g$ or less, specifically, 0.10 $cm^3/g$ or more to 1.0 $cm^3/g$ or less. Further, the diameter of pores in the isomerization catalyst may be 2.0 to 120 nm, specifically 3.0 to 100 nm.

Here, the volume of pores represents the volume of all pores included in one of the isomerization catalysts and the diameter of pores represents the average diameter of all pores included in one of the isomerization catalysts, which can be measured with a general measuring instrument using the nitrogen adsorption method.

Amount of Catalyst and Reactant Used

In the isomerization of CHDA according to the one embodiment, the amount of the isomerization catalyst used can be appropriately controlled in accordance with the content of CHDA containing the cis isomer which is a reactant. Specifically, as the content of the isomerization catalyst is higher relative to CHDA, the reaction rate increases. Therefore, in the isomerization method of CHDA according to an embodiment of the present disclosure, the isomerization catalyst may be added in an amount such that the weight ratio of the isomerization catalyst/CHDA is 0.1 or more. However, when the content of the isomerization catalyst relative to CHDA is above a certain level, considering that the effect of increasing the reaction rate relative to the amount used is slight and the reaction efficiency decreases, the isomerization catalyst can be added, more specifically, in an amount such that the weight ratio of the isomerization catalyst/CHDA satisfies 0.1 to 2.0. If the weight ratio of the isomerization catalyst/CHDA is less than 0.1, it is difficult to obtain a sufficient isomerization effect, and when the weight ratio exceeds 2.0, the increase in reaction efficiency may be slight as compared to the amount of catalyst used as described above. Considering the effect of improving the reaction rate and increasing the yield of t-CHDA by controlling the weight ratio of the isomerization catalyst/CHDA, the isomerization catalyst may be more preferably added in an amount such that the weight ratio of the isomerization catalyst/CHDA is 0.14 to 1.67, more specifically, 0.14 to 1.0 or 0.14 to 0.83.

Meanwhile, the isomerization method of CHDA according to an embodiment of the present disclosure using the above-mentioned isomerization catalyst utilizes a mixed solution prepared by mixing CHDA containing a cis isomer, water, and an isomerization catalyst.

The CHDA may include only the cis isomer, or may further contain the trans isomer in addition to the cis isomer. When it further contains a trans isomer, in order to obtain a sufficient isomerization effect, the content thereof may be preferably less than 50% by weight, more specifically 40% by weight or less, based on the total weight of CHDA.

The mixed solution is prepared by dissolving CHDA and a catalyst in water, wherein in order to increase the solubility of CHDA and further increase the isomerization efficiency, an alkaline metal, an alkaline earth metal, a basic aqueous solution or the like may be further added, or a stirring step or the like may be optionally further performed.

Moreover, the concentration of CHDA in the mixed solution affects the isomerization reaction of CHDA. Specifically, as the concentration of CHDA decreases, the reaction rate of the isomerization reaction increases. However, when the concentration of CHDA is too low, there is a possibility that the production and yield of t-CHDA is reduced and the reaction efficiency is lowered, and when the concentration of CHDA is too high, the reaction rate is reduced, which may make it difficult to obtain a sufficient isomerization effect. Thus, in the isomerization method of CHDA according to an embodiment of the present disclosure, the concentration of CHDA may be 0.5 to 30% by weight based on the total weight of the mixed solution. When the concentration of CHDA is less than 0.5% by weight, the production amount and yield of the product are too low and thus, the efficiency is low. On the other hand, when the concentration of CHDA exceeds 30% by weight, there is a possibility that the reaction rate is slower, the preparation process is longer, and the isomerization effect is lowered. In addition, there is a possibility that a high concentration of CHDA is precipitated in a solid phase. More specifically, the concentration of CHDA in the mixed solution may be 0.8 to 20 wt %, or 0.8 to 6.5 wt %. Considering the effect of increasing the reaction rate and increasing the yield of t-CHDA by controlling the concentration of CHDA, it may be preferably 0.8 to 3.5 wt %, or 0.8 to 3.2 wt %.

After the addition of the isomerization catalyst, the isomerization reaction occurs when the mixed solution is heat-treated by a method such as heating. At this time, the reaction rate can be adjusted by controlling the reaction temperature. Specifically, as the reaction temperature increases during the isomerization reaction, the reaction rate also increases. When the reaction temperature exceeds a certain level, it may be difficult to control the reaction rate. Thus, in the isomerization method of CHDA according to an embodiment of the present disclosure, a step of heat-treating the reaction system in a temperature range of 220 to 280° C. is performed after adding the isomerization catalyst. If the temperature during the isomerization reaction is less than 220° C., the reaction rate is slow, and if the temperature is greater than 280° C., it may be difficult to control the reaction rate. Considering the effect of increasing the reaction rate and improving the yield of t-CHDA by controlling the reaction temperature, the heat treatment step may be more preferably performed at 230 to 270° C., more specifically at 250 to 270° C.

Further, a stirring step may be performed during the isomerization reaction, and by controlling the speed during the stirring step, it is possible to increase the reaction efficiency during the isomerization reaction. Specifically, the stirring step may be performed at a speed of 500 to 2000 rpm, and more specifically, it may be preferably performed at a speed of 700 to 1300 rpm or 1000 to 1300 rpm.

Meanwhile, the stirring step may be performed using a conventional stirring device.

It may be more preferable in terms of process efficiency that the isomerization reaction is performed for 2 to 5 hours under the condition where all the above isomerization reaction conditions are satisfied.

8

Composition Containing Isomerized Cyclohexane Dicarboxylic Acid (Mixture of t-CHDA and c-CHDA with High t-CHDA Content)

In another embodiment of the present disclosure, a composition comprising cyclohexane dicarboxylic acid isomerized by the method described above is provided.

This composition was obtained as a result of performing an isomerization reaction of CHDA mainly containing c-CHDA by using a catalyst containing zirconia and having a BET specific surface area of 50 m$^2$/g or more, which is a composition comprising CHDA with a high content of t-CHDA.

Specifically, when using a catalyst containing zirconia but having a BET specific surface area of less than 50 m$^2$/g, the initial reaction rate of the isomerization reaction is low, and the yield of t-CHDA may remain at a level of 60% or less.

On the other hand, when using a catalyst containing zirconia and having a BET specific surface area of 50 m$^2$/g or more, it has a wider BET specific surface area, so that the initial reaction rate of the isomerization reaction is improved, and the yield of t-CHDA can be as high as 63% or more.

In addition, as described above, as the amount of weak acid sites and the amount of middle acid sites of the isomerization catalyst are larger, and the total amount of acid sites resulting therefrom is larger, the isomerization reaction of CHDA according to the one embodiment is further promoted, and thus the final yield of t-CHDA can be improved.

According to actual tests about this, the more catalysts containing zirconia, having a BET specific surface area of 50 m$^2$/g or more, and having the total amount of acid sites of 400 umol/g$_{cat}$ a or more, 500 umol/g$_{cat}$ c or more, 600 umol/g$_{cat}$ c or more, 700 umol/g$_{cat}$ or more, or 750 umol/g$_{cat}$ or more, are used, the yield of t-CHDA resulting from the isomerization of CHDA can be increased to 63 wt % or more, 63.5 wt % or more, 64 wt % or more, 64.5 wt % or more, or 65 wt % or more.

For reference, the yield of t-CHDA may be expressed as mol % of c-CHDA converted to t-CHDA through an isomerization reaction, based on the amount (100 mol %) of c-CHDA contained in the CHDA reactant before the isomerization reaction. However, the CHDA reactant before the isomerization reaction mainly contains c-CHDA, the content (mol %) of t-CHDA relative to the total molar amount of CHDA obtained after the isomerization reaction can be represented as the yield of t-CHDA.

In other words, the content of the trans isomer may be 63% by weight or more, 63.5% or more, 64% or more, 64.5% or more, or 65% or more in the total cyclohexane dicarboxylic acid in the composition of the embodiment.

Further, according to the above-described one embodiment, by using the above isomerization catalyst, it is possible to easily increase and adjust the trans content in CHDA, and there is no concern about the occurrence of side reactions.

Therefore, the composition of the embodiment can be used as a raw material for pharmaceuticals, synthetic resins, synthetic fibers, or dyes.

Hereinafter, the present disclosure will be described in more detail by way of examples. However, the following examples are for illustrative purposes only, and are not intended to limit the scope of the present disclosure. In addition, in the following examples and comparative examples, "%" and "part" indicating the content are based on weight unless otherwise specified.

Example 1

For the isomerization reaction of CHDA, a batch reactor capable of withstanding 300° C. and 150 bar was selected as the reactor. 4.05 g of CHDA containing the cis isomer, 1.125 g of zirconia (monoclinic) from Saint-Gobain, and 250 g of distilled water as the solvent were placed in the prepared batch reactor, and the temperature of the mixed solution was raised to 250° C. while string at 50 rpm (concentration of CHDA in solution: 1.6 wt %, weight ratio of zirconia/CHDA=0.28). When the temperature of the mixed solution reached 250° C., the stirring speed was increased to 1000 rpm, and the reaction was carried out for 5 hours while stirring.

The BET specific surface area, pore volume, and average pore diameter of zirconia (monoclinic) used herein are as shown in Table 1 below, and acid characteristics are as shown in Table 2 below.

Example 2

The procedure was performed in the same manner as in Example 1 except that zirconia (monoclinic) from Johnson Matthey was used instead of zirconia (monoclinic) from Saint-Gobain used in Example 1.

Example 3

The procedure was performed in the same manner as in Example 1 except that zirconia (monoclinic)-titania (anatase) from Saint-Gobain, in which the content of titania (anatase) in the total amount (100 wt %) of the mixture was 41 wt %, was used instead of zirconia (monoclinic) from Saint-Gobain used in Example 1.

Example 4

The procedure was performed in the same manner as in Example 1 except that zirconia-lanthania (tetragonal) from Saint-Gobain, in which the content of lanthania (tetragonal) in the total amount (100 wt %) of the mixture was 8.3 wt %, was used instead of zirconia (monoclinic) from Saint-Gobain used in Example 1.

Example 5

The procedure was performed in the same manner as in Example 1 except that zirconia-yttria (tetragonal) from Saint-Gobain, in which the content of yttria (tetragonal) in the total amount (100 wt %) of the mixture was 7.3 wt %, was used instead of zirconia (monoclinic) from Saint-Gobain used in Example 1.

Comparative Example 1

The procedure was performed in the same manner as in Example 1 except that zirconia (monoclinic) from CNVI-SION Co., Ltd. was used instead of zirconia (monoclinic) from Saint-Gobain used in Example 1.

Comparative Example 2

The procedure was performed in the same manner as in Example 1 except that zirconia (monoclinic) from Kanto Chemical was used instead of zirconia (monoclinic) from Saint-Gobain used in Example 1.

Test Example 1: Catalyst Analysis

In order to select a catalyst optimized for the isomerization reaction of c-CHDA to t-CHDA, not only the composition and crystal structure of the catalyst, but also the total pore volume, the average pore diameter, and the acid content at each acid site and the total acid amount contained therein will be comprehensively reviewed.

In this regard, prior to the isomerization reaction test, the following analysis was performed for each catalyst of Examples 1 to 5 and Comparative Examples 1 and 2.

(1) XRD

In order to confirm the crystal structure of each catalyst of Examples 1 to 5 and Comparative Examples 1 and 2, X-ray diffraction analysis with Cu Kα was performed, and the results are shown in FIG. 1 and Table 1.

(2) BET Specific Surface Area

For each catalyst of Examples 1 to 5 and Comparative Examples 1 and 2, the specific surface area was evaluated from the amount of nitrogen gas adsorbed under liquid nitrogen temperature (77K) by using a BET specific surface area measuring device (manufacturer BEL Japan, device name: BELSORP_Mini), and the evaluation results are shown in Table 1.

(3) Average Pore Diameter and Volume

For each catalyst of Examples 1 to 5 and Comparative Examples 1 and 2, the adsorption amount was measured up to a relative pressure (P/P0) of 1 under a liquid nitrogen temperature (77K) and the desorption amount up to 0.03 by using a BET specific surface area measuring device (manufacturer BEL Japan, device name: BELSORP_Mini), which were used to measure the average pore diameter and volume from the BJH formula, and the results are shown in Table 1.

(4) $NH_3$-TPD

To investigate the acid characteristics of each catalyst of Examples 1 to 5 and Comparative Examples 1 and 2, the ammonia-temperature programmed desorption ($NH_3$-TPD) analysis was performed, and the results are shown in Table 2 and FIG. 2 The specific analysis method is as follows.

0.2 g of each of the catalysts of Examples 1 to 5 and Comparative Examples 1 and 2 was taken and placed in a quartz reactor, and pretreated at 150° C. for 1 hour under helium at a rate of 20 ml/min. After cooling to room temperature, the adsorption amount of ammonia on the catalyst surface was saturated using 15% ammonia/helium gas.

And, in order to remove the physically adsorbed ammonia, vacuum treatment was performed at 150° C. for 1 hour. Then, while raising the temperature to 900° C. at a rate of 10° C. per minute, the amount of ammonia desorbed under helium at a rate of 10 ml/min was measured with an $NH_3$-TPD device (AutoChem 2920) equipped with a gas chromatography detector, and the temperature programmed desorption curve was shown in FIG. 2.

In FIG. 2, each catalyst of Examples 1 to 5 and Comparative Examples 1 and 2 had two or three peaks, which was classified into weak, middle and strong acid sites from the low temperature region, and the amount of $NH_3$ desorbed at each acid site was calculated from the area of each peak, and is shown in Table 2 below.

TABLE 1

| | Composition | Crystal structure | BET specific area $(m^2/g)$ | Pore volume $(cm^3/g)$ | Average pore diameter (nm) |
|---|---|---|---|---|---|
| Comparative Example 1 | $ZrO_2$ | Monoclinic | 27 | 0.27 | 50.4 |
| Comparative Example 2 | $ZrO_2$ | Monoclinic | 6 | 0.08 | 58.1 |
| Example 1 | $ZrO_2$ | Monoclinic | 103 | 0.30 | 10.8 |
| Example 2 | $ZrO_2$ | Monoclinic | 100 | 0.14 | 3.3 |
| Example 3 | 41% $TiO_2$—$ZrO_2$ | Monoclinic $ZrO_2$ and anatase $TiO_2$ | 86.8 | 0.46 | 37.6 |
| Example 4 | 8.3% $La_2O_3$—$ZrO_2$ | Tetragonal | 114 | 0.25 | 38.8 |
| Example 5 | 7.3% $Y_2O_3$—$ZrO_2$ | Tetragonal | 134 | 0.25 | 98.0 |

TABLE 2

| | Acid content at weak acid sites $(umol/g_{cat})$ | Acid content at middle acid sites $(umol/g_{cat})$ | Acid content at strong acid sites $(umol/g_{cat})$ | Total acid amount $(umol/g_{cat})$ |
|---|---|---|---|---|
| Comparative Example 1 | 40 | 184 | 0 | 224 |
| Comparative Example 2 | 14 | 30 | 0 | 44 |
| Example 1 | 299 | 575 | 0 | 874 |
| Example 2 | 106 | 668 | 10 | 784 |
| Example 3 | 416 | 165 | 58 | 639 |
| Example 4 | 140 | 733 | 28 | 901 |
| Example 5 | 152 | 663 | 162 | 977 |

In Table 1 above, it can be confirmed that since a larger amount of reactants is adsorbed onto the catalysts of Examples 1 to 5, which have a wider BET specific surface area, relative to the catalysts of Comparative Examples 1 and 2, it is possible to contribute to the improvement of reaction efficiency.

On the other hand, it is known that as the weak acid sites and the middle acid sites of the catalyst are larger, the isomerization reaction of CHDA is more remarkably promoted, and thus the conversion rate of the reactant to the product is improved.

Looking at Table 2 above from this point of view, the catalysts of Examples 1 to 5 have a large amount of weak acid sites and a large amount of middle acid sites as compared to the catalysts of Comparative Examples 1 and 2, the total amount of acid sites resulting therefrom is significantly large, and that the isomerization reaction of CHDA is further promoted, so that it is expected that it can contribute to the improvement of the yield of t-CHDA.

Test Example 2: Evaluation of Catalytic Effect on Isomerization Reaction of CHDA Actually, to evaluate the effect of the catalyst on the isomerization reaction of CHDA, after completion of the isomerization reaction using each catalyst of Examples 1 to 5 and Comparative Examples 1 and 2, the content of t-CHDA was measured, respectively. The mol % of c-CHDA converted to t-CHDA through the isomerization reaction among the amount (100 mol %) of c-CHDA contained in the CHDA reactant is shown as the yield in FIG. 3.

According to FIG. 3, it can be confirmed that when the catalysts of Examples 1 to are used, the yield of t-CHDA due to the isomerization reaction is significantly increased as compared with the catalysts of Comparative Examples 1 and 2.

Specifically, when the catalyst of Comparative Example 2 was used, the yield of t-CHDA was less than 50%, and when the catalyst of Comparative Example 1 was used, the yield of t-CHDA remained at the level of 60%.

Here, the catalysts of Comparative Examples 1 and 2 are monoclinic zirconia, and the crystal structure and composition thereof are the same. However, it can be seen that in the catalyst of Comparative Example 1, which had similar average pore diameters, but high pore volume, BET specific surface area, the acid content at each acid site, and the total acid amount, the yield of t-CHDA was partially increased as compared with Comparative Example 2.

However, it is confirmed that the catalysts of Examples 1 and 2 are also monoclinic zirconia, and the crystal structure and composition thereof are the same as those of Comparative Examples 1 and 2, but the initial reaction efficiency and the yield of t-CHDA are significantly improved as compared with Comparative Examples 1 and 2.

It is inferred that two factors acted on this. Specifically, the catalysts of Examples 1 and 2 had a wider BET specific surface area than Comparative Examples 1 and 2, and thus the initial reaction rate could be improved. In addition, the catalysts of Examples 1 and 2 is larger in terms of the acid content at weak acid sites, the acid content at middle acid sites, and the total acid amount resulting therefrom, as compared with Comparative Examples 1 and 2, so that the isomerization reaction of CHDA can proceed at a lower reaction temperature, and a higher yield of t-CHDA (about 65% or more) can be achieved.

On the other hand, comparing Examples 1 to 5, it is confirmed that the BET specific surface area and the acid characteristics have a great influence on reaction efficiency and t-CHDA yield, rather than the crystallinity of the catalyst, the pore volume inside the catalyst, and the average pore size.

Specifically, zirconia may have various crystal structures of monoclinic, tetragonal, or hexagonal systems, zirconia having a monoclinic crystal structure can be selected as the catalyst if only thermal and chemical stability are considered.

However, Examples 4 and 5 include tetragonal zirconia, but use a catalyst compounded with tetragonal lanthania or tetragonal yttria. Although they have disadvantages in thermal and chemical stability, they have a wider BET specific surface area than Comparative Examples 1 and 2 using a catalyst containing monoclinic zirconia alone. Due to the catalytic properties with high total acid amount, it exhibits better initial reaction efficiency and achieves higher t-CHDA yield.

In this regard, even if tetragonal zirconia, which has lower thermal and chemical stability than monoclinic, is contained as a component of the catalyst, it can be seen that as the compounding with heterogeneous transition metal oxides, the BET specific surface area characteristics, the acid characteristics, or the like are appropriately adjusted, better reaction efficiency and t-CHDA yield can be achieved than a catalyst containing monoclinic zirconia alone.

In addition, in the case of Example 3 using a catalyst in which monoclinic zirconia and anatase titania are compounded, due to the catalytic characteristics that the BET specific surface area is large and the total acid amount is large, more excellent thermal reaction efficiency and t-CHDA yield can be achieved as compared with Comparative Examples 1 and 2.

The invention claimed is:

1. An isomerization method of a cyclohexane dicarboxylic acid, comprising: heat-treating a mixed solution prepared by mixing a cyclohexane dicarboxylic acid containing a cis isomer, water, and an isomerization catalyst to isomerize the cis isomer to a trans isomer, wherein the isomerization catalyst contains zirconia and has a BET specific surface of 50 m$^2$/g or more and 140 m$^2$/g or less, and wherein:

the isomerization catalyst has a total amount of acid sites of 400 umol/g$_{cat}$ or more as measured by an ammonia-temperature programmed desorption (NH$_3$-TPD) method.

2. The isomerization method according to claim 1, wherein:

the isomerization catalyst is composed of acid sites such that, based on the total amount of acid sites (100 mol %) measured by the ammonia-temperature programmed desorption (NH$_3$-TPD), the amount of weak acid sites with an acid site desorption temperature of 50 to 150° C. is 5 to 75 mol %, the amount of middle acid sites with an acid site desorption temperature of 150 to 450° C. is 15 to 95 mol %, and the amount of strong acid sites with an acid site desorption temperature of 450° C. or more corresponds to the rest.

3. The isomerization method according to claim 1, wherein:

the zirconia in the isomerization catalyst is a monoclinic zirconia, a tetragonal zirconia, or a mixture thereof.

4. The isomerization method according to claim 1, wherein:

the isomerization catalyst further comprises a heterogeneous transition metal oxide.

5. The isomerization method according to claim 4, wherein:

the isomerization catalyst is a titania-zirconia composite, a lanthania-zirconia composite, an yttria-zirconia composite, or a mixture thereof.

6. The isomerization method according to claim 4, wherein:

a content of the heterogeneous transition metal oxide is 1 to 50% by weight, based on the total amount (100% by weight) of the isomerization catalyst.

7. The isomerization method according to claim 1, wherein:

the isomerization catalyst comprises pores therein, and a volume of the pores is 0.05 cm$^3$/g or more and 1.5 cm$^3$/g or less.

8. The isomerization method according to claim 1, wherein:

the isomerization catalyst comprises pores therein, and a diameter of the pores is 2.0 to 120 nm.

9. The isomerization method according to claim 1, wherein:

the cyclohexane dicarboxylic acid containing the cis isomer is contained in an amount of 0.5 to 30% by weight based on the total amount (100% by weight) of the mixed solution.

10. The isomerization method according to claim 1, wherein:

the isomerization catalyst is added in an amount that achieves the weight ratio of the isomerization catalyst to the cyclohexane dicarboxylic acid (the weight ratio of the isomerization catalyst/cyclohexane dicarboxylic acid) of 0.1 or more and 2.0 or less.

11. The isomerization method according to claim 1, wherein:

the heat treatment is performed at 220 to 350° C.

* * * * *